United States Patent [19]
Pastorello

[11] Patent Number: 5,831,144
[45] Date of Patent: Nov. 3, 1998

[54] REFRIGERATION COMPRESSOR OIL TESTING PROCESS AND APPARATUS

[76] Inventor: John Pastorello, 2572 Fender Ave. #C, Fullerton, Calif. 92831

[21] Appl. No.: 846,241

[22] Filed: Apr. 28, 1997

[51] Int. Cl.[6] .................................................. G01N 31/22
[52] U.S. Cl. ...................... 73/23.2; 73/31.05; 73/61.41; 422/86; 422/58; 62/125
[58] Field of Search .................................. 73/23.2, 29.04, 73/31.05, 29.01, 61.41, 61.44, 64.56, 53.01; 422/86, 58, 56, 57; 436/41, 42; 62/125, 127, 129

[56] References Cited

U.S. PATENT DOCUMENTS

| | | | |
|---|---|---|---|
| 4,917,863 | 4/1990 | Bather | 422/58 |
| 4,923,806 | 5/1990 | Klodowski | 436/39 |
| 4,946,649 | 8/1990 | Pannwitz | 422/60 |
| 5,069,879 | 12/1991 | Leichnitz et al. | 422/86 |
| 5,071,768 | 12/1991 | Klodowski | 436/39 |
| 5,174,964 | 12/1992 | Klodowski | 422/88 |
| 5,186,899 | 2/1993 | Drago et al. | 422/104 |
| 5,419,177 | 5/1995 | Pastorello | 73/23.4 |
| 5,538,690 | 7/1996 | Greer et al. | 422/86 |

*Primary Examiner*—Michael Brock
*Attorney, Agent, or Firm*—Edgar W. Averill, Jr.

[57] ABSTRACT

A process and apparatus for determining the amount of contamination in the lubricant phase of a refrigeration system. The process utilizes a clear glass tube which contains an inert substance such as glass beads coated with a solvatochromic compound, preferably the solvatochromic compound is a mixture of Benzophenoxazine and Benzophenoxazone. A sample of the lubricant to be tested is passed into the glass tube and passes over the glass beads, picking up a portion of the solvatochromic compound. A white absorbent material such as sterile cellulose is positioned adjacent the coated substrate and the color reaction between the lubricant and the solvatochromic compound is clearly evident on the white absorbent material which then can be compared with a standard set of colors to determine the amount of the contamination.

10 Claims, No Drawings

REFRIGERATION COMPRESSOR OIL TESTING PROCESS AND APPARATUS

THE FIELD OF THE INVENTION

The field of invention is refrigeration system servicing, and more particularly a detector tube assay employing a solvatochromic indicator for use in refrigeration system servicing.

BACKGROUND OF THE INVENTION

Refrigeration fluids are split into two phases, first the refrigerant phase, which is typically a low boiling point fluorocarbon gas, liquid or vapor, and secondly the oil phase, which can be either a mineral, alkylbenzene, polyol ester or polyalkylene glycol lubricant. Applicant is the inventor of a refrigerant gas contamination detector kit shown in U.S. Pat. No. 5,419,177. The specification of this '177 patent is incorporated by reference herein.

The '177 patent relates to detector tube analysis of contaminants in a refrigerant gas under pressure. The present invention specifies a detector tube for determining the level of contaminates that are present in the oil phase.

In general, both phases will exhibit some degree of contamination in the form of water since it is nearly impossible to purify or render the fluids fully anhydrous. Although not desirable, water is always incidental and inherently present. Water levels that exceed 10 ppm as measured in the refrigerant phase or water levels that exceed 50 ppm as measured in the oil phase can undergo hydrolysis to form detrimental acids when subjected to the heat and compression of refrigeration equipment cycling. Typically a high moisture content will promote inorganic acids to form out of the refrigerant and organic acids to form out of the lubricants over the working life of the refrigeration system. Neglect and the lack of preventative maintenance in the detection of high moisture and acid formation are conditions that can lead to premature compressor or other associated refrigeration component failures.

Obtaining an oil sample for testing can be very labor intense. For example, the service technician must remove anywhere from 1 to 50 milliliters of oil from a compressor crankcase of a sealed system. Since most all compressors of the hermetic variety have no oil tap or drain plug, the equipment must be taken off line and opened. This involves the removal and recovery of the pressurized refrigerant gas in the system, removal and inversion of the compressor to pour out an oil sample for testing; then reinstallation of the compressor, complete evacuation of the system and finally recharging with refrigerant gas for eventual equipment start-up and on-line duty.

Laboratory sample submission for quantitative acid and/or moisture analysis is generally too impractical for the average service technician versus the availability of an instant on-site test.

PRIOR ART

Traditionally, field test methods for determining the acid content of the oil phase of a refrigeration system is limited to pH indicators. Typically, the test kit contains a pH dye such as Bromophenol Blue or other pH indicating solutions or strips. The problems with the use of pH indicators in refrigeration diagnostics are bountiful, in that, (1) the pH range of indicator dyes are too broad, (2) a definitive end point (color change) may be masked or buffered by certain oil additives, (3) the oil type being tested may exhibit solubility problems with the test solution or strip, (4) moisture levels are not indicated, and (5) pH dyes are more reliable with aqueous media than with organic solvents.

With the advent of solvatochromic chemistry, a more accurate and reliable field test for oil contamination is possible. However, the solvatochromic dyes of the Pyridium-N-Phenol Betaines, described in U.S. Pat. Nos. 4,677,076, 4,677,079 and 4,722,983 failed due to their lack of distinct or discernable color differentiation in the visible range when small shifts in solution polarity must be quantified. The Pyridium-N-Phenol Betaines along with the classic solvatochromics of the Indoanilines, Carbonylpyridiums and Nitroanilines all require the use of sensitive colorimetric instruments to measure differences in color intensity.

SUMMARY OF THE INVENTION

It is the object of the present invention to provide a more definitive oil phase test which will be easy to use in the field and provide better quantitative results relative to the degree of contaminants therein. The oil phase test is preferred but not limited to a detector tube assay being of the same construction and/or adaptability to the detector tube holding device described in U.S. Pat. No. 5,419,177 which is incorporated herein by reference.

The specification for an indicator material shall be formulated with a dye or dye combination of the solvatochromic Benzophenoxazine - Benzophenoxazone compounds.

This invention in particular relates to compounds and/or materials that will exhibit color transitions or separations when small shifts in the polarity of a solvent must be determined. Specifically, but not limited to, refrigeration compressor oil that becomes more polar due to moisture, acid, dissolved metals or other aggressive polar adulterants.

DETAILED DESCRIPTION OF THE INVENTION

Solvatochromism is expected when the oil polarity has undergone change. Assume that a virgin anhydrous oil or nearly anhydrous oil represents the ground state; then a more excited state can be induced by the addition of adulterants such as water, acid, base and/or other aggressive ionic materials.

A small group of dyes are known to undergo color transition with changes in solution polarity and these dyes may be tailored to act as a probe. Ideally, the probe will be sensitive enough to promote a definite, distinguishable color transition from the ground state, stepwise to higher polar states. The color transitions specific for this invention must be readily identifiable in the visual range since the average service technician is not familiar with the application and use of colorimetric instrumentation.

The best suited solvatochromic dyes for this invention were determined by exhaustive chemical screening. It was discovered that the best dye candidates belong to the Benzophenoxazine and/or Benzophenoxazone families having the basis structure:

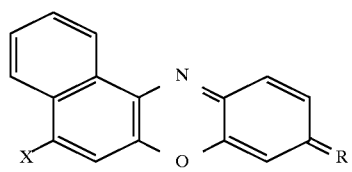

When X is an amine, alkyl amine or dialkylamine group and R is an alkyl amine or dialkylamine containing 1–10 carbon atoms, derivatives of the Benzophenoxazine family are represented.

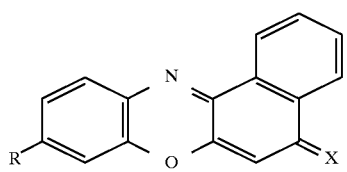

When X is an oxygen and R is alkylamine or dialkylamine containing 1–10 carbon atoms, derivatives of the Benzophenoxazone group are represented.

The Benzophenoxazines are typically prepared by reacting 5-diethyl amino-2 nitrosophenol with 1-naphthylamine. The Benzophenoxazones are formed by refluxing the Benzophenoxazine with sulfuric acid.

The oxazine compounds can be treated with a hydroxide, chloride or sulfonated to form radical salts.

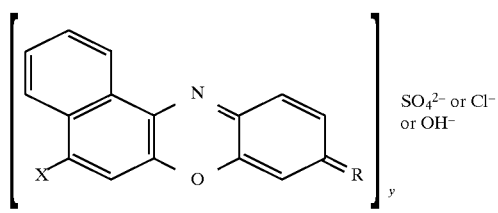

y=1 when treated with a Chloride or Hydroxide
y=2 when Sulfonated

The radical salts offer similar degrees of solvatochromism, but can exhibit different degrees of solubility with the target solvents. A salt must be chosen that will dissolve in the target solvent/solvents in order for a solvatochromic effect to occur. A radical salt of the Benzophenoxazine can be tailored to exhibit more or less solubility characteristics for the target solvent. The ratio of Benzophenoxazine to Benzophenoxazone may be adjusted to limit or broaden the solvatochromic property's range or effect.

Experimentally then, each oxazine and oxazone dye can be dissolved in various organic oils or solvents. Coloration of the oil or solvent will vary based on the minute' differences in polarity. For example, a purified non-polar solvent represents a ground state and would exhibit a light coloration, while a more polar solvent representing a more excited state would exhibit a darker color.

In practice, the lubricants listed below are the most conventional and predominate oils used in the refrigeration industry to date:

Mineral Oil (MO)
Alkylbenzene (AB)
Polyol Ester (POE)
Polyalkylene Glycol (PAG)

Virgin samples of the above oils were obtained and allowed to dry for one week over anhydrous silica gel, then passed through a column containing Brockman I activated alumina. The results from Karl Fischer titrations on the dried solvents indicated that the water content of the liquids did not exceed 5 ppm. The oils now represent a near ground state. Alloquats from each oil were then adulterated with the addition of various amounts of water, acid and combinations of water and acid that would typically be found in operating refrigeration compressors and thereby represent different excited states. It should be noted that the acidic component was a 50/50 mixture of hydrochloric and oleic acids which are the two most predominate acids of formation within a refrigeration system.

The solvatochromic oxazine and oxazone dyes of the radical hydroxide form were allowed to dissolve, in each near ground state oil respectively, and the color change noted:

GROUND STATE OIL TEST

| | With Oxazine | Oxazone | Oxazine + Oxazone |
|---|---|---|---|
| MO | no color | pale yellow | bright yellow |
| AB | pale yellow | yellow | yellow/brown |
| POE | yellow/orange | orange | orange |
| PAG | orange | orange | pink |

The natural order of polarity of these solvents are ascending, being that MO is nonpolar, AB is slightly polar, POE is moderately polar and PAG is the most polar solvent. A definite solvatochromic shift is confirmed with the dyes and dye combinations by the distinctive color transition from no color to yellow to orange to a weak red (pinkish).

An extensive study was conducted to determine which individual dye or dye combination would give the best color resolution as well as a definitive stepwise color transition with adulterated oils. All the trial and error data revealed that a combination of oxazine and oxazone were far superior for color differentiation when each isolated dye or dye derivative was tested.

The optimum dye mixture was mainly composed of the radical hydroxide oxazine with a counter balance of from 0.001 to 0.010% oxazone, where about 0.005% oxazone is preferred.

The test observations when 0.04 grams of the optimized solvatochromic dye is dissolved in 100 grams of the adulterated oils below.

CONTAMINATED OIL TEST

| | 25 ppm water | 40 ppm water | 90 ppm water | 25 ppm water 10 ppm acid | 40 ppm water 25 ppm acid | 50 ppm water 25 ppm acid | 90 ppm water 50 ppm acid | 150 ppm water 100 ppm acid |
|---|---|---|---|---|---|---|---|---|
| MO | yel | org | mag | pink | lav | mag | vio | blue |
| AB | yel | org | mag | pink | lav | mag | vio | blue |
| POE | org | pink | mag | pink | lav | mag | vio | blue |
| PAG | org | pink | mag | pink | lav | mag | vlo | blue |

It can be concluded that a nearly quantitative solvatochromic shift, yellow to orange to pink to lavender to magenta to violet to blue, is established. A subjective evaluation is forwarded being that a color less than magenta being yellow, orange, pink or lavender would indicate that an acceptable amount of water-acid contamination is present in the bulk lubricating oil, and any color intensity magenta or greater being magenta, violet or blue would indicate a highly polar and adverse condition within the bulk lubricant. The criteria for the pass/fail scenario is in alliance with the standards set forth by the refrigeration industry, where the threshold limit for water should not exceed 50 ppm and the sum of acid plus water be less than 70 ppm in totality.

It should be noted that it is the amount of oxazone a component (about 0.005%) added into the dominate oxazine dye formulation that balances the final color scheme. Addition of excess oxazone will cause greater red shifts while insufficient or when no oxazone is incorporated blue/violet shifts occur too prematurely with initially more polar POE and PAG solvents.

It is conceivable that an oil or solvent be charged with a solvatochromic dye or dye complex in order to monitor the condition of the oil or solvent over time. Such applications may be useful in determining when to change the oil or solvent in air compressors, vacuum pumps or other internally lubricated mechanisms. Or, if it is not desirable to charge the oil or solvent with dye, a small sample of oil could be externally tested with a strip or solution containing the dye.

A detector tube construction for sampling oil directly from a sealed refrigeration system is forwarded herein, since a detector tube assay offers an instant evaluation of the oil phase without disassembly or operating downtime.

Experimentally, 0.05 to 0.25% solution of the oxazine/oxazone dye was dissolved in anhydrous methanol, with 0.10% being preferred. The solution was coated onto an inert substrate such as powdered borosilicate glass and the alcohol and any associated water was evaporated off with heat in a dry box circulating dry nitrogen gas.

Into a 3.5" 1×5/32" diameter detector tube, a dry and sterile acrylic bating was compacted to a length of ½" assembled in the same dry box. About a 2" fill of the dye coated powdered glass was then packed above the acrylic batting. The detector tube ends were then sealed with rubber stoppers as to conform to the construction of a detector described under the previous patent.

The sealed detector tube was removed from the box and inserted into a detector tube holding device (see U.S. Pat. No. 5,419,177, FIGS. 2–7, and columns 2–4) that was connected to the suction (return line) service port of an operating refrigeration system. It is known that small amounts of oil will be carried with the circulating refrigerant gas, and by connection to the service port, refrigerant gas and trace amounts of oil will bleed through the detector tube. It should be noted that the amount of oil necessary to obtain a good test result could be as small as 10 microliters. A de minimis bleed for about 15 seconds caused trace amounts of oil to enter into the detector tube, flushed through the dye substrate and deposited an orange stain onto -the acrylic batting. The contaminant level of the oil was known prior to the test to contain 35 ppm water and less than 0.10 ppm acid. Thus, the result was consistent with laboratory trials from a representative sample.

Subsequent testing on many other refrigeration systems also yielded results that consistently correlated with the lab data. Experimentally, the dye a was coated onto a variety of other different substrates in attempts to find the most suitable substrate. Any substrate that had a polar character performed less satisfactorily than those that were non-polar or otherwise highly inert. Different fabric or stain enhancing materials were substituted for the acrylic batting. Sterile cellulose, cotton, wool and non-polar polymer fabrics worked satisfactorily with the natural fabrics being preferred due to their more permanent color fastness to a dye wash. Some ion exchange resins were also tested with satisfactory results.

The specific detector tube arrangement therefore consists of a solvatochromic dye of the Benzophenoxazine and/or Benzophenoxazone groups coated onto a substrate which is upflow from a stainable media, developer or indicating layer. Oil is allowed to enter the tube, come in contact with and wash through the dye segment and then stain a second segment. The resultant color which is retained by the second segment indicates the polarity of the oil being sampled. The endpoint color can then be visually matched to a color chart for a semi-quantitative analysis.

The present embodiments of this invention are thus to be considered in all respects as illustrative and not restrictive; the scope of the invention being indicated by the appended claims rather than by the foregoing description. All changes which come within the meaning and range of equivalency of the claims are intended to be embraced therein.

I claim:

1. A color sensitive process for determining the amount of contamination in a lubricant sample comprising:

passing a lubricant sample over a carrier containing a color sensitive chemical, said color sensitive chemical being reactive with said lubricant depending upon the degree of contamination of said lubricant to provide a colored reactant solution;

conveying the colored reactant solution into an inert, white carrier held within a clear tube;

observing the resulting colored reactant on said inert white carrier; and comparing the color with a color standard to determine the amount of contamination in said lubricant sample.

2. The color sensitive process of claim 1 wherein said carrier is selected from the group consisting of glass beads, paper, polymer, and resin gels.

3. The color sensitive process of claim 1 wherein said inert white carrier is selected from the group consisting of acrylic batting, sterile cellulose, wool, resin, paper, polymers and gels.

4. A process for determining the amount of contamination of a lubricant sample comprising the steps of:

coating an inert substrate with a solvatochromic dye selected from the group consisting of Benzophenoxazine and Benzophenoxazone to produce a coated substrate;

positioning the coated substrate within the interior of a clear tube having an entrance end and an exit end;

placing a white absorbent material adjacent said coated substrate and between said coated substrate and said exit end;

introducing a sample of the lubricant into the entrance end of said clear tube;

passing a gaseous carrier stream into the entrance end to move the sample of lubricant through said coated substrate and into said white absorbent material to produce a colored substrate portion; and viewing the resulting color of the colored substrate portion which provides a measure of the contamination of the lubricant sample.

5. The process of claim 4 wherein said inert substrate is selected from the group consisting of glass beads, polymer, resin, paper fiber and gel.

6. The process of claim 4 wherein said white absorbent material is selected from the group consisting of acrylic batting, sterile cellulose, cotton and wool.

7. A article useful for determining the amount of contamination in a sample of lubricant taken from an air conditioning system, said tube comprising:

a clear, hollow elongated member having an entrance end and an exit end;

an inert carrier material coated with a solvatochromic chemical held within said clear, hollow elongated member near the entrance end thereof; and a white absorbent material held within said clear, hollow elongated member adjacent said inert carrier material and positioned between said inert carrier material and the exit end of said clear, hollow elongated member.

8. The article of claim 7 wherein said inert carrier material is glass beads.

9. The article of claim 7 wherein said solvatochromic chemical is selected from the group consisting of Benzophenoxazine and Benzophenoxazone.

10. The article of claim 7 wherein said white absorbent material is selected from the group consisting of acrylic batting, sterile cellulose, cotton, wool, polymer, gel, paper, resin or the like.

* * * * *